United States Patent
Sani et al.

(10) Patent No.: US 11,821,309 B2
(45) Date of Patent: Nov. 21, 2023

(54) RESERVOIR STAGING INDEX (RSI)

(71) Applicant: Saudi Arabian Oil Company, Dhahran (SA)

(72) Inventors: Abu Mohammed A. Sani, Dhahran (SA); Maytham I. Ismail, Anak (SA); Mohd Azizi Ibrahim, Buqayq (SA); Clovis Satyro Bonavides, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 263 days.

(21) Appl. No.: 17/182,635

(22) Filed: Feb. 23, 2021

(65) Prior Publication Data

US 2022/0268154 A1  Aug. 25, 2022

(51) Int. Cl.
*E21B 49/08* (2006.01)
*E21B 43/25* (2006.01)
*G01N 33/24* (2006.01)
*G01V 11/00* (2006.01)

(52) U.S. Cl.
CPC ............ *E21B 49/087* (2013.01); *E21B 43/25* (2013.01); *G01N 33/24* (2013.01); *G01V 11/00* (2013.01); *E21B 2200/20* (2020.05)

(58) Field of Classification Search
CPC ... E21B 49/087; E21B 2200/20; G01N 33/24; G01V 11/00
See application file for complete search history.

(56) References Cited

U.S. PATENT DOCUMENTS

| | | | |
|---|---|---|---|
| 10,400,590 B1* | 9/2019 | Aldred | E21B 49/00 |
| 2013/0140031 A1* | 6/2013 | Cohen | E21B 43/26 |
| | | | 166/308.1 |
| 2018/0238147 A1* | 8/2018 | Shahri | G06F 17/18 |
| 2019/0292905 A1 | 9/2019 | Ross et al. | |

OTHER PUBLICATIONS

Sala et al., "Integrated Advanced Workflows and Heterogeneity Analysis for Planning Unconventional Horizontal Wells in Western Desert of Egypt," Offshore Mediterranean Conference and Exhibition, Ravenna, Italy, Mar. 2017 (Year: 2017).*

(Continued)

*Primary Examiner* — Mischita L Henson
(74) *Attorney, Agent, or Firm* — Fish & Richardson P.C.

(57) ABSTRACT

Systems and methods include a method for determining perforation cluster points of a reservoir. A rock type of a geological formation of a reservoir is determined using petrophysical data. The transmissible sublayers of the reservoir are determined by grouping the petrophysical data into different subset transmissible layers based on cut-off criteria. Net transmissible reservoir footage for the transmissible sublayers are generated based on averages of parameters for minimum and maximum measured depths. Potential stages for the reservoir are determined using a conditional formatting on the transmissible reservoir footage. Potential perforation cluster points selected based on the potential stages for the reservoir are received from input of an engineer.

20 Claims, 3 Drawing Sheets

(56) References Cited

OTHER PUBLICATIONS

Egbele et al., "Net-to-Gross Ratios: Implications in Integrated Reservoir Management Studies," SPE 98808, presented at the 29th Annual SPe International Technical Conference and Exhibition, Abuha, Nigeria, Aug. 1-3, 2005, 12 pages (Year: 2005).*

"What is the Lyell Collection," Lyell Collection, the Geological Society, available on or before 2012, 1 page.

Egbele et al., "Net-to-Gross Ratios: Implications in Integrated Reservoir Management Studies," SPE 98808, presented at the 29th Annual SPE International Technical Conference and Exhibition, Abuha, Nigeria, Aug. 1-3, 2005, 12 pages.

Mahbaz et al., "Optimization of reservoir cut-off parameters: a case study in SW Iran," Petroleum Geoscience, 2011, 17:355-363.

* cited by examiner

RESERVOIR STAGING INDEX (RSI)

BACKGROUND

Technical Field

The present disclosure applies to stage selection of a well.

Background

The targeted conventional selection of potential stages in a well can result in poor quality stages for which it may be difficult to inject fluid or initiate a fracture. Improvements in stage selection can result in increased gas production (for example, by avoiding costs of non-injectable stages) and can reduce operational time of a well.

SUMMARY

The present disclosure describes techniques that can be used for reservoir stage selection. In some implementations, a computer-implemented method includes the following. A rock type of a geological formation of a reservoir is determined using petrophysical data. Transmissible sublayers of the reservoir are determined by grouping the petrophysical data into different subset transmissible layers based on cut-off criteria. Net transmissible reservoir footage for the transmissible sublayers are generated based on averages of parameters for minimum and maximum measured depths. Potential stages for the reservoir are determined using a conditional formatting on the transmissible reservoir footage. Potential perforation cluster points selected based on the potential stages for the reservoir are received from input of an engineer.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented instructions stored on the non-transitory, computer-readable medium.

The subject matter described in this specification can be implemented in particular implementations, so as to realize one or more of the following advantages. The present disclosure solves the problem of selecting tight zones in which it is difficult to achieve injectivity. Techniques of the present disclosure can also eliminate human random error of the stage selection by different engineers through the introduction of a uniform, consistent, and standardized process. The processes can be machine-based with less human interaction, while still providing a window for optimization of the selection based on an engineer's experience and the history of the offset wells in the area. Implementation of the techniques can be used for all new drilled wells before looking at the processed log data, as a quick-look can introduce machine/data process selection to the entire stimulation stage selection process. This can ensure all parameters (including petrophysical and geomechanical properties) in the log are taken into consideration effectively. These techniques can solve deficiencies of conventional techniques that lack the use of rock type injectivity models and rely on high human interaction, which can lead to inconsistent and different selections by different engineers. Improvements provided by techniques of the present disclosure can provide the advantage of a machine selection process that significantly reduces the need for human interaction. Further, the incorporation of a rock type injectivity model can provide rock quality in terms of injectivity and stimulation. The techniques can integrate the petrophysical and geomechanical characterization of a reservoir, while considering reservoir performance and stimulation methodology practices to pick the best potential stimulation stages. Machine-based processes can be faster by reducing human interactions, which can reduce the time spent by engineers on the selection of stages. The techniques can provide uniformity and consistency in a standard process of initializing stage selection, making overall stage selection processes more efficient. The techniques are less prone to human error because of the machine-based interface. The interface includes a window for an engineer to optimize the selection process, and the system systematically identifies the injectable zones.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

Figure 1:
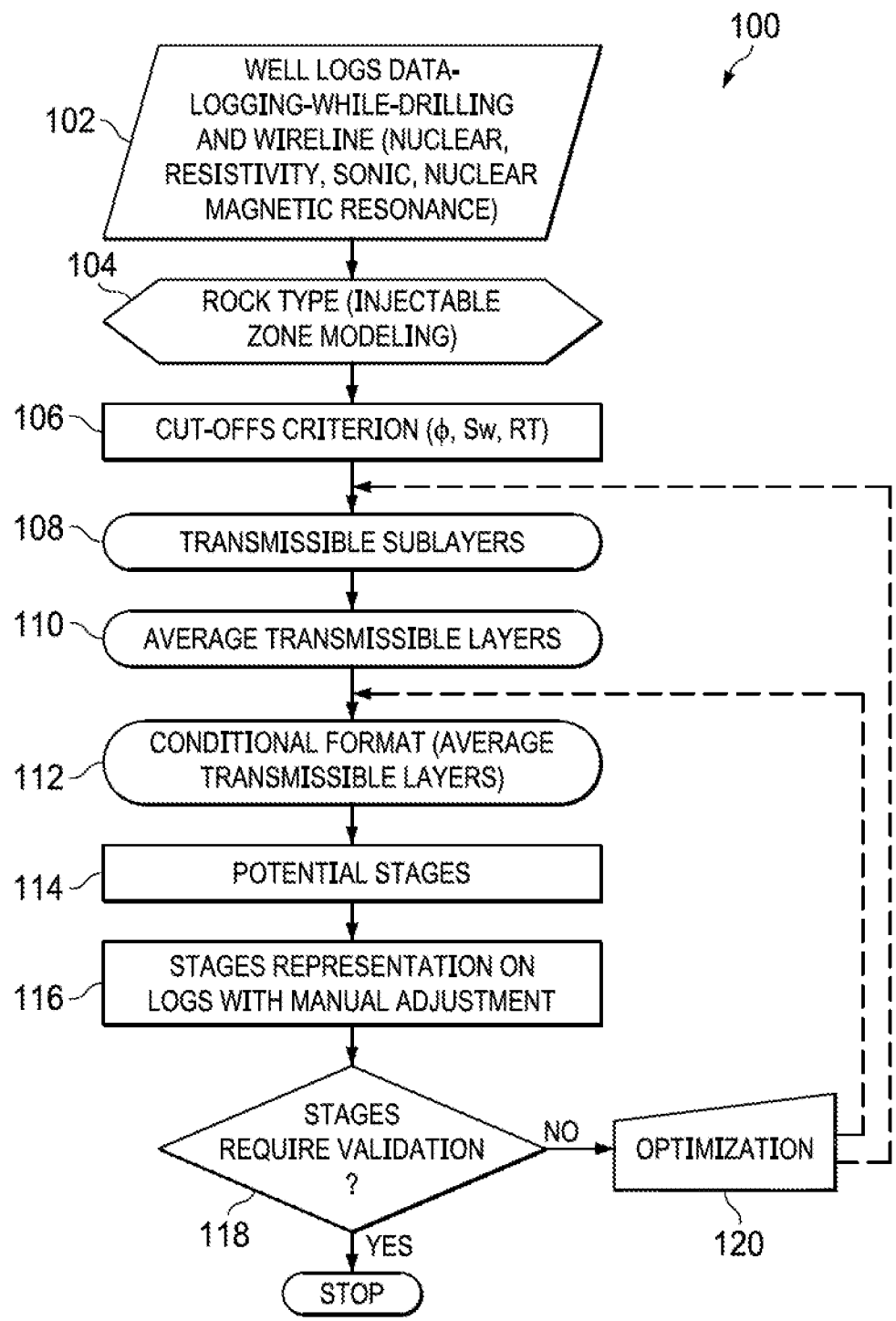
FIG. 1 is a flow diagram showing an example of a process workflow for reservoir staging index, according to some implementations of the present disclosure.

The following detailed description describes techniques for reservoir stage selection. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

In some implementations, a workflow can be developed that utilizes existing petrophysical properties and rock typing to generate transmissible layers of similar properties. These transmissible layers can then be combined to provide transmissible intervals. The transmissible intervals can then be grouped into stages depending on the lateral footage. The intervals can indicate the best positions to locate perforations to aid with injectivity and to eventually stimulate successfully. The workflow can ensure a machine standardized approach in picking perforations and stages without significant human interaction.

The workflow process can be based on the use of well logs data (that includes processed rock type information from logs data) and filters the data to obtain transmissible layers, which are then averaged into single layers. Conditional formatting can then be applied to the identified layers and the rock type to determine potential stages. The process can be optimized on the basis of an engineer's knowledge of the field and the planned stimulation requirements.

The aim of the workflow can include making stage selection for stimulation requirements efficient, uniform, consistent, and standardized across, for example, an entire gas reservoir management department. The process can be machine-based with reduced human interaction, while providing a window for an engineer to optimize the selection process.

In some implementations, experimentation can be used to improved processes. For example, conventional techniques for choosing stages with a greater dependency on φ and Sw are not sufficient enough and the inclusion of rock type presents several sections where φ is high and Sw is low, yet the quality of the rock may be poor and with a very low degree of injectivity in this case the techniques of the present disclosure can reduce or eliminate potential tight zones.

Experimentation can determine that the consistency and accuracy of the process are very high. The processed involved can be repeatable, provided that the sequence of established workflow are followed. During experimentation, in all the cases that the workflow process was applied, the reservoir staging index (RSI) stages provided a number of stages close to the final agreed conventional manual selected stages, including accounting for stage spacing, the number of clusters, and the plug depth to make the stimulation operation possible. Wells used in experimentation were completed in a carbonate reservoir and were spread across an entire field. Diagnostics studies can be conducted that involved production-logging, tracers, temperature logs, and microseismic data to verify the quality of the RSI selection process on the basis of stage-by-stage performance in order to make it the standard practical application for a petroleum company.

FIG. 1 is a flow diagram showing an example of a process workflow 100 for reservoir staging index, according to some implementations of the present disclosure.

A Rock Type step 104 includes a process of generating the rock type. For example, a rock typing process can be used that includes defining and identifying threshold values for injectable zone quality. The rock type provides a qualitative measure on the potential of the rock to be stimulated and for likely good performance. In some implementations, generating the rock type can include the following steps for determining a rock testability index (RTI). Petrophysical data of a geological formation at a particular rate is received. The petrophysical data is measured at each depth of a plurality of depths from a surface of the Earth. For each depth of the plurality of depths, an RTI is determined for the geological formation. The RTI indicates a probability of success for performing a hydrocarbon fluid formation test at each depth. The RTI is generated by normalizing a rock type of the geological formation. The RTI is adjusted based on a correspondence of the petrophysical data to hydrocarbon productivity. A display device generates a visual representation of the RTI at the particular rate. The visual representation indicates a potential hydrocarbon productivity of the geological formation. Techniques for generating the rock type can include techniques described in U.S. Pat. No. 10,890,066, filed Aug. 28, 2019, and hereby incorporated by reference in its entirety.

A Cut-offs Criterion step 106 involves applying the standard approved cut-offs criteria of φ and Sw for khuff and pre-khuff reservoirs. The rock type criterion based on offset performance is equally applied with porosity, Sw, and intrinsic permeability cutoffs as well.

A Transmissible Sublayers step 108 of the process involves identification and grouping of the data into different subset transmissible layers on the basis of satisfying the cut-offs criteria defined above. This process is subject to rock type optimization based on the nature of the field, the reservoir, and the performance of the offset wells in the area. The results are summarized in Table 1, including caliper minus bitsize (CALI DCA), compressional wave delay time (DTCO), shear wave delay time (DTSM), intrinsic permeability (PERM), effective porosity (PHIE), bulk density (RHOB), effective water saturation (SWE), thermal neutron porosity (TNPH), and true vertical depth (TVD).

TABLE 1

Transmissible Layers

| Trans Sub Layers | DEPTH | CALI DCA | DTCO | DTSM | PERM | PHIE | RHOB | SWE | TNPH | Rock Type | TVD |
|---|---|---|---|---|---|---|---|---|---|---|---|
| 1 | xx000.0 | 6.69 | 55.76 | 97.13 | 0.7077 | 0.1094 | 2.64 | 0.0461 | 0.0906 | 4 | yyy54.2 |
| 1 | xx000.5 | 6.67 | 55.71 | 95.90 | 0.5185 | 0.0994 | 2.64 | 0.0517 | 0.0879 | 3 | yyy54.2 |
| 1 | xx001.0 | 6.65 | 54.99 | 93.49 | 0.4890 | 0.0971 | 2.66 | 0.0524 | 0.0852 | 3 | yyy54.3 |
| 1 | xx001.5 | 6.62 | 53.38 | 91.44 | 0.3437 | 0.0864 | 2.69 | 0.0588 | 0.0825 | 3 | yyy54.4 |
| 1 | xx007.0 | 6.65 | 52.79 | 94.83 | 0.4666 | 0.0978 | 2.67 | 0.0553 | 0.0953 | 3 | yyy55.0 |
| 1 | xx007.5 | 6.67 | 52.44 | 94.53 | 0.4629 | 0.0975 | 2.69 | 0.0558 | 0.0953 | 3 | yyy55.1 |
| 2 | xx050.0 | 6.47 | 54.67 | 98.88 | 0.6474 | 0.1164 | 2.69 | 0.0517 | 0.1209 | 3 | yyy60.2 |
| 2 | xx055.0 | 6.71 | 52.39 | 95.97 | 0.4074 | 0.0988 | 2.74 | 0.0649 | 0.0995 | 3 | yyy60.8 |
| 3 | xx137.0 | 6.30 | 50.53 | 88.36 | 0.2020 | 0.0752 | 2.80 | 0.0709 | 0.0705 | 3 | yyy71.9 |
| 3 | xx137.5 | 6.30 | 50.30 | 88.68 | 0.1665 | 0.0745 | 2.80 | 0.0844 | 0.0707 | 3 | yyy72.0 |
| 3 | xx138.0 | 6.30 | 50.17 | 88.64 | 0.1683 | 0.0740 | 2.80 | 0.0815 | 0.0708 | 3 | yyy72.1 |
| ... | ... | ... | ... | ... | ... | ... | ... | ... | ... | ... | ... |

In a Well Logs Data step 102, logging-while-drilling (LWD) provides resistivity, density, and neutron porosity data which is processed to get the petrophysical data. LWD, sonic, nuclear magnetic resonance (NMR), Nuclei, Facies, and wire line (WL) data are used to generate the rock type.

In an Average Transmissible Layers step 110, the data obtained for the sublayers obtained from step 108 are averaged for each layer to get an average (avg) representative values for minimum (min) and maximum (max) measured depth (MD), and to generate the net transmissible (Trans) reservoir footage.

TABLE 2

Average Representative Values

| Trans Layers | Min MD | Max MD | Avg PHIE | Avg SWE | Avg PERM | Avg Rock Type | Before Net | Net Trans Reservoir (ft) | After Net (ft) |
|---|---|---|---|---|---|---|---|---|---|
| 1 | xx000.0 | xx007.5 | 0.4981 | 0.0979 | 0.0534 | 3.2 |  | 8.0 | 42.5 |
| 2 | xx050.0 | xx055.0 | 0.5274 | 0.1076 | 0.0583 | 3.0 | 42.5 | 5.5 | 82.0 |
| 3 | xx137.0 | xx263.0 | 1.4869 | 0.1307 | 0.0629 | 4.6 | 82.0 | 126.5 | 45.0 |
| 4 | xx308.0 | xx351.5 | 0.9789 | 0.1332 | 0.0581 | 5.2 | 45.0 | 44.0 | 16.0 |
| 5 | xx367.5 | xx389.0 | 0.4975 | 0.1184 | 0.0860 | 4.3 | 16.0 | 22.0 | 14.0 |
| 6 | xx403.0 | xx610.5 | 0.7888 | 0.1251 | 0.0687 | 5.0 | 14.0 | 208.0 | 10.5 |
| 7 | xx621.0 | xx642.5 | 0.5102 | 0.1258 | 0.0859 | 3.8 | 10.5 | 22.0 | 407.0 |
| 8 | xy049.5 | xy231.0 | 0.7172 | 0.1508 | 0.0941 | 5.9 | 407.0 | 182.0 | 27.0 |
| 9 | xy258.0 | xy611.5 | 0.3830 | 0.1209 | 0.1458 | 5.3 | 27.0 | 354.0 | 29.0 |
| 10 | xy640.5 | xy723.0 | 0.1840 | 0.0886 | 0.1652 | 6.5 | 29.0 | 83.0 |  |
| ... | ... | ... | ... | ... | ... | ... | ... | ... | ... |

In a Conditional Format step 112, an application occurs of a conditional formatting satisfying a given criterion for the rock type and the net transmissible reservoir footage to obtain the potential stages.

TABLE 3

Potential Stages

| Trans Layers | Min MD | Max MD | Avg PHIE | Avg SWE | Avg PERM | Avg Rock Type | Before Net | Net Trans Reservoir (ft) | After Net Trans | Potential Stages |
|---|---|---|---|---|---|---|---|---|---|---|
| 3 | xx137.0 | xx263.0 | 1.4869 | 0.1307 | 0.0629 | 4.6 | 82.0 | 126.5 | 45.0 | Yes |
| 4 | xx308.0 | xx351.5 | 0.9789 | 0.1332 | 0.0581 | 5.2 | 45.0 | 44.0 | 16.0 | Yes |
| 6 | xx403.0 | xx610.5 | 0.7888 | 0.1251 | 0.0687 | 5.0 | 14.0 | 208.0 | 10.5 | Yes |
| 8 | xy049.5 | xy231.0 | 0.7172 | 0.1508 | 0.0941 | 5.9 | 407.0 | 182.0 | 27.0 | Yes |
| 9 | xy258.0 | xy611.5 | 0.3830 | 0.1209 | 0.1458 | 5.3 | 27.0 | 354.0 | 29.0 | Yes |
| 10 | xy640.5 | xy723.0 | 0.1840 | 0.0886 | 0.1652 | 6.5 | 29.0 | 83.0 | 48.0 | Yes |
| 18 | xz102.5 | xz137.5 | 0.0522 | 0.0652 | 0.2127 | 5.1 | 76.5 | 35.5 | 25.5 | Yes |
| 23 | xz516.0 | xz547.5 | 0.0518 | 0.0709 | 0.2513 | 3.5 | 42.0 | 32.0 | 49.0 | Yes |
| 44 | yy984.5 | yy032.5 | 0.0618 | 0.0686 | 0.2033 | 5.0 | 154.0 | 48.5 | 76.0 | Yes |
| 49 | yz406.0 | yz446.5 | 0.0927 | 0.0821 | 0.1922 | 4.0 | 32.0 | 41.0 | 25.5 | Yes |
| ... | ... | ... | ... | ... | ... | ... | ... | ... | ... | ... |

In a Potential Stages step 114, once potential stages have been obtained from step 112, an engineer can use a copy of the well logs and then use the RSI to stage the well and pick potential perforation cluster points. The workflow has clusters criterion incorporated to determine the number of clusters that would be required to effectively stimulate the stage. This step also requires optimization by the engineer based on his experience in the field and of the reservoir. The engineer can also utilize the history of offset wells' completion and performance to adjust for stage length, number of clusters, and the clusters' position relative to the transmissible net reservoir coverage.

TABLE 4

Potential Perforation Cluster Points

| Trans Layers | Min MD | Max MD | Avg PHIE | Avg SWE | Avg PERM | Avg ROCK TYPE | Before Net | Net Trans Reservoir (feet) | After Net Trans | Potential Stages | Clusters | Stages |
|---|---|---|---|---|---|---|---|---|---|---|---|---|
| 3 | xx137.0 | xx263.0 | 1.4869 | 0.1307 | 0.0629 | 4.6 | 82.0 | 126.5 | 45.0 | Yes | 3 | 1 |
| 4 | xx308.0 | xx351.5 | 0.9789 | 0.1332 | 0.0581 | 5.2 | 45.0 | 44.0 | 16.0 | Yes | 3 | 2 |
| 6 | xx403.0 | xx610.5 | 0.7888 | 0.1251 | 0.0687 | 5.0 | 14.0 | 208.0 | 10.5 | Yes | 3 | 3 |
| 8 | xy049.5 | xy231.0 | 0.7172 | 0.1508 | 0.0941 | 5.9 | 407.0 | 182.0 | 27.0 | Yes | 3 | 4 |
| 9 | xy258.0 | xy611.5 | 0.3830 | 0.1209 | 0.1458 | 5.3 | 27.0 | 354.0 | 29.0 | Yes | 4 | 5 |
| 10 | xy640.5 | xy723.0 | 0.1840 | 0.0886 | 0.1652 | 6.5 | 29.0 | 83.0 | 48.0 | Yes | 3 | 6 |
| 18 | xz102.5 | xz137.5 | 0.0522 | 0.0652 | 0.2127 | 5.1 | 76.5 | 35.5 | 25.5 | Yes | 3 | 7 |
| 23 | xz516.0 | xz547.5 | 0.0518 | 0.0709 | 0.2513 | 3.5 | 42.0 | 32.0 | 49.0 | Yes | 3 | 8 |
| 44 | yy984.5 | yy032.5 | 0.0618 | 0.0686 | 0.2033 | 5.0 | 154.0 | 48.5 | 76.0 | Yes | 3 | 9 |
| 49 | yz406.0 | yz446.5 | 0.0927 | 0.0821 | 0.1922 | 4.0 | 32.0 | 41.0 | 25.5 | Yes | 3 | 10 |
| ... | ... | ... | ... | ... | ... | ... | ... | ... | ... | ... | ... | ... |

In a Stages Representation on Logs step 116, the potential stages obtained are put on the well logs and are followed with conventional manual adjustment to meet the staging requirement in terms of stage spacing, number of clusters, and plug depth to enable smooth stimulation operations.

TABLE 5

Manual Adjustments

| | RSI | | | | Manual Selection | | | |
|---|---|---|---|---|---|---|---|---|
| Stages | Top | Bottom | Clusters | Match | Top | Bottom | Clusters | Stages |
| 10 | xx137.0 | xx263.0 | 3 | —> | xx000 | xx300 | 3 | 10 |
| 9 | xx308.0 | xx351.5 | 3 | | | | | |
| 8 | xx403.0 | xx610.5 | 3 | —> | xx300 | xx700 | 3 | 9 |
| 7 | xy049.5 | xy231.0 | 3 | —> | xx700 | xy300 | 3 | 8 |
| 6 | xy258.0 | xy611.5 | 4 | —> | xy300 | xy800 | 3 | 7 |
| 5 | xy640.5 | xy723.0 | 3 | | | | | |
| 4 | xz102.5 | xz137.5 | 3 | —> | xy800 | xz200 | 3 | 6 |
| 3 | xz516.0 | xz547.5 | 3 | —> | xz200 | xz900 | 5 | 5 |
| | | | | | xz900 | yy900 | 3 | 4 |
| 2 | yy984.5 | yy032.5 | 3 | | | | | |
| 1 | yz406.0 | yz446.5 | 3 | —> | yy900 | yz700 | 4 | 3 |
| | | | | | yz700 | zz200 | 3 | 2 |
| | | | | | zz200 | zz500 | 3 | 1 |

In a Validation decision step 118, a determination is made whether the stages require validation. If validation is not needed, then the process workflow 100 can stop. Otherwise, optimization would be needed.

In an Optimization step 120, the optimization process involves adjusting one or both of the criterion for transmissible sublayers and the conditional formatting of the average transmissible layers to satisfy the stimulation requirement. The basis for the optimization include the offset wells' performance and the overall well plan that includes the stimulation plan. After optimization, the process workflow 100 can resume at step 112.

Experimentation and study can find that the traditional method of choosing stages with more dependency on $\phi$ and Sw is not sufficient. Also, the inclusion of rock type presented several sections where the $\phi$ is high and Sw low, but the quality of the rock is poor and with very low degree of injectivity. In this area, the techniques of the present disclosure can be used to reduce/eliminate potential tight zones. Experimentation and study can find that consistency and accuracy of the disclosed techniques to be very high. Moreover, the results from the process are repeatable provided the sequence of the workflow is followed.

Figure 2:
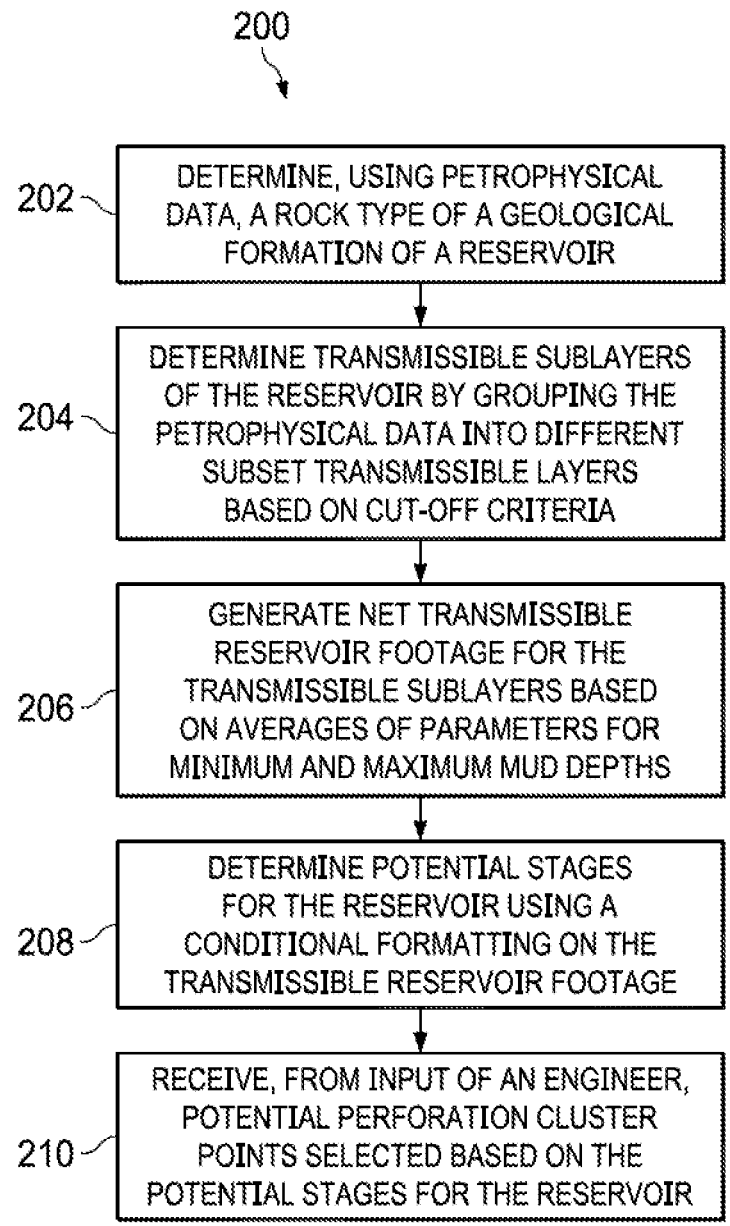
FIG. 2 is a flowchart of an example of a method for performing reservoir staging index, according to some implementations of the present disclosure.

FIG. 2 is a flowchart of an example of a method 200 for performing reservoir staging index, according to some implementations of the present disclosure. For clarity of presentation, the description that follows generally describes method 200 in the context of the other figures in this description. However, it will be understood that method 200 can be performed, for example, by any suitable system, environment, software, and hardware, or a combination of systems, environments, software, and hardware, as appropriate. In some implementations, various steps of method 200 can be run in parallel, in combination, in loops, or in any order.

At 202, a rock type of a geological formation of a reservoir is determined using petrophysical data. For example, determining the petrophysical data can include processing LWD data to include resistivity data, density data, and neutron porosity data. From 202, method 200 proceeds to 204.

At 204, transmissible sublayers of the reservoir are determined by grouping the petrophysical data into different subset transmissible layers based on cut-off criteria. For example, transmissible layers can be selected as described with reference to Table 1. From 204, method 200 proceeds to 206.

At 206, net transmissible reservoir footage for the transmissible sublayers are generated based on averages of parameters for minimum and maximum measured depths. For example, average representative values as shown in Table 2 can be generated. From 206, method 200 proceeds to 208.

At 208, potential stages for the reservoir are determined using a conditional formatting on the transmissible reservoir footage. For example, potential stages as shown in Table 3 can be generated. From 208, method 200 proceeds to 210.

At 210, potential perforation cluster points selected based on the potential stages for the reservoir are received from input of an engineer. For example, user selections can be received through a graphical user interface to arrive at potential perforation cluster points shown in Table 4. After 210, method 200 can stop.

In some implementations, method 200 further includes a clusters presentation and review interface. For example, an engineer can be presented (for example, in a graphical user interface) with a history of offset wells' completion and performance to adjust for stage length, a number of clusters, and clusters' positions relative to a transmissible net reservoir coverage defined by the transmissible reservoir footage. The number of clusters required to effectively stimulate stages of the reservoir can be provided for presentation to the engineer. The engineer can make changes to the number of clusters as needed. For example, manual adjustments to the number of clusters can be received from input of the engineer to meet staging requirement in terms of stage spacing, number of clusters, and plug depth to enable smooth stimulation operations.

In some implementations, method 200 further includes determining whether the potential stages need validation. In response to determining that the potential stages need validation, performing an optimization on the transmissible layers.

Figure 3:
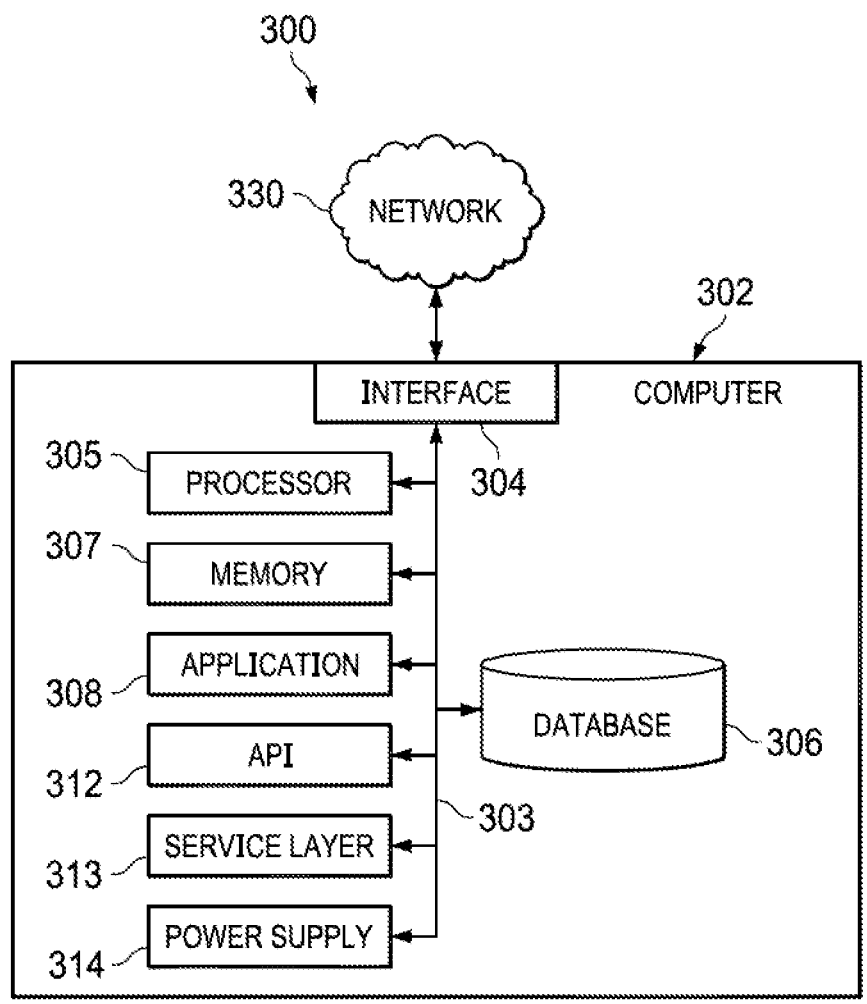
FIG. 3 is a block diagram illustrating an example computer system used to provide computational functionalities associated with described algorithms, methods, functions, processes, flows, and procedures as described in the present disclosure, according to some implementations of the present disclosure.

FIG. 3 is a block diagram of an example computer system 300 used to provide computational functionalities associated with described algorithms, methods, functions, processes, flows, and procedures described in the present disclosure, according to some implementations of the present disclosure. The illustrated computer 302 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 302 can include input devices such as keypads, keyboards, and touch screens that can accept user information. Also, the computer 302 can include output devices that can convey information associated with the operation of the computer 302. The information can include digital data, visual data, audio information, or a combination of information. The information can be presented in a graphical user interface (UI) (or GUI).

The computer 302 can serve in a role as a client, a network component, a server, a database, a persistency, or components of a computer system for performing the subject matter described in the present disclosure. The illustrated computer 302 is communicably coupled with a network 330. In some implementations, one or more components of the computer 302 can be configured to operate within different environments, including cloud-computing-based environments, local environments, global environments, and combinations of environments.

At a top level, the computer 302 is an electronic computing device operable to receive, transmit, process, store, and manage data and information associated with the described subject matter. According to some implementations, the computer 302 can also include, or be communicably coupled with, an application server, an email server, a web server, a caching server, a streaming data server, or a combination of servers.

The computer 302 can receive requests over network 330 from a client application (for example, executing on another computer 302). The computer 302 can respond to the received requests by processing the received requests using software applications. Requests can also be sent to the computer 302 from internal users (for example, from a command console), external (or third) parties, automated applications, entities, individuals, systems, and computers.

Each of the components of the computer 302 can communicate using a system bus 303. In some implementations, any or all of the components of the computer 302, including hardware or software components, can interface with each other or the interface 304 (or a combination of both) over the system bus 303. Interfaces can use an application programming interface (API) 312, a service layer 313, or a combination of the API 312 and service layer 313. The API 312 can include specifications for routines, data structures, and object classes. The API 312 can be either computer-language independent or dependent. The API 312 can refer to a complete interface, a single function, or a set of APIs.

The service layer 313 can provide software services to the computer 302 and other components (whether illustrated or not) that are communicably coupled to the computer 302. The functionality of the computer 302 can be accessible for all service consumers using this service layer. Software services, such as those provided by the service layer 313, can provide reusable, defined functionalities through a defined interface. For example, the interface can be software written in JAVA, C++, or a language providing data in extensible markup language (XML) format. While illustrated as an integrated component of the computer 302, in alternative implementations, the API 312 or the service layer 313 can be stand-alone components in relation to other components of the computer 302 and other components communicably coupled to the computer 302. Moreover, any or all parts of the API 312 or the service layer 313 can be implemented as child or sub-modules of another software module, enterprise application, or hardware module without departing from the scope of the present disclosure.

The computer 302 includes an interface 304. Although illustrated as a single interface 304 in FIG. 3, two or more interfaces 304 can be used according to particular needs, desires, or particular implementations of the computer 302 and the described functionality. The interface 304 can be used by the computer 302 for communicating with other systems that are connected to the network 330 (whether illustrated or not) in a distributed environment. Generally, the interface 304 can include, or be implemented using, logic encoded in software or hardware (or a combination of software and hardware) operable to communicate with the network 330. More specifically, the interface 304 can include software supporting one or more communication protocols associated with communications. As such, the network 330 or the interface's hardware can be operable to communicate physical signals within and outside of the illustrated computer 302.

The computer 302 includes a processor 305. Although illustrated as a single processor 305 in FIG. 3, two or more processors 305 can be used according to particular needs, desires, or particular implementations of the computer 302 and the described functionality. Generally, the processor 305 can execute instructions and can manipulate data to perform the operations of the computer 302, including operations using algorithms, methods, functions, processes, flows, and procedures as described in the present disclosure.

The computer 302 also includes a database 306 that can hold data for the computer 302 and other components connected to the network 330 (whether illustrated or not). For example, database 306 can be an in-memory, conventional, or a database storing data consistent with the present disclosure. In some implementations, database 306 can be a combination of two or more different database types (for example, hybrid in-memory and conventional databases) according to particular needs, desires, or particular implementations of the computer 302 and the described functionality. Although illustrated as a single database 306 in FIG. 3, two or more databases (of the same, different, or combination of types) can be used according to particular needs, desires, or particular implementations of the computer 302 and the described functionality. While database 306 is illustrated as an internal component of the computer 302, in alternative implementations, database 306 can be external to the computer 302.

The computer 302 also includes a memory 307 that can hold data for the computer 302 or a combination of components connected to the network 330 (whether illustrated or not). Memory 307 can store any data consistent with the present disclosure. In some implementations, memory 307 can be a combination of two or more different types of memory (for example, a combination of semiconductor and magnetic storage) according to particular needs, desires, or particular implementations of the computer 302 and the described functionality. Although illustrated as a single memory 307 in FIG. 3, two or more memories 307 (of the same, different, or combination of types) can be used according to particular needs, desires, or particular implementations of the computer 302 and the described functionality. While memory 307 is illustrated as an internal component of the computer 302, in alternative implementations, memory 307 can be external to the computer 302.

The application 308 can be an algorithmic software engine providing functionality according to particular needs, desires, or particular implementations of the computer 302 and the described functionality. For example, application 308 can serve as one or more components, modules, or applications. Further, although illustrated as a single application 308, the application 308 can be implemented as multiple applications 308 on the computer 302. In addition, although illustrated as internal to the computer 302, in alternative implementations, the application 308 can be external to the computer 302.

The computer 302 can also include a power supply 314. The power supply 314 can include a rechargeable or non-rechargeable battery that can be configured to be either user- or non-user-replaceable. In some implementations, the power supply 314 can include power-conversion and management circuits, including recharging, standby, and power management functionalities. In some implementations, the power-supply 314 can include a power plug to allow the computer 302 to be plugged into a wall socket or a power source to, for example, power the computer 302 or recharge a rechargeable battery.

There can be any number of computers 302 associated with, or external to, a computer system containing computer 302, with each computer 302 communicating over network 330. Further, the terms "client," "user," and other appropriate terminology can be used interchangeably, as appropriate, without departing from the scope of the present disclosure. Moreover, the present disclosure contemplates that many users can use one computer 302 and one user can use multiple computers 302.

Described implementations of the subject matter can include one or more features, alone or in combination.

For example, in a first implementation, a computer-implemented method includes the following. A rock type of a geological formation of a reservoir is determined using petrophysical data. Transmissible sublayers of the reservoir are determined by grouping the petrophysical data into different subset transmissible layers based on cut-off criteria. Net transmissible reservoir footage for the transmissible sublayers are generated based on averages of parameters for minimum and maximum measured depths. Potential stages for the reservoir are determined using a conditional formatting on the transmissible reservoir footage. Potential perforation cluster points selected based on the potential stages for the reservoir are received from input of an engineer.

The foregoing and other described implementations can each, optionally, include one or more of the following features:

A first feature, combinable with any of the following features, where determining the petrophysical data includes processing logging-while-drilling (LWD) data to include resistivity data, density data, and neutron porosity data.

A second feature, combinable with any of the previous or following features, where the method further includes: providing, for presentation to the engineer, a history of offset wells' completion and performance to adjust for stage length, a number of clusters, and clusters' positions relative to a transmissible net reservoir coverage defined by the transmissible reservoir footage; and providing, for presentation to the engineer, the number of clusters required to effectively stimulate stages of the reservoir.

A third feature, combinable with any of the previous or following features, where the method further includes receiving, from input of the engineer, manual adjustments to the number of clusters to meet staging requirement in terms of stage spacing, number of clusters, and plug depth to enable smooth stimulation operations.

A fourth feature, combinable with any of the previous or following features, where the method further includes determining whether the potential stages need validation.

A fifth feature, combinable with any of the previous or following features, where the method further includes: in response to determining that the potential stages need validation, performing an optimization on the transmissible layers.

A sixth feature, combinable with any of the previous or following features, where determining the rock type includes determining a rock testability index (RTI) including: receiving, by a computer system, petrophysical data of the geological formation at a particular rate, the petrophysical data measured at each depth of a plurality of depths from a surface of the Earth; for each depth of the plurality of depths, determining, using the computer system, a rock testability index (RTI) for the geological formation, the RTI indicating a probability of success for performing a hydrocarbon fluid formation test at each depth, the determining of the RTI including: generating, using the computer system, the RTI, the generating including normalizing a rock type of the geological formation; and adjusting, using the computer system, the RTI based on a correspondence of the petrophysical data to hydrocarbon productivity; and generating, using a display device of the computer system, a visual representation of the RTI at the particular rate, the visual representation indicating a potential hydrocarbon productivity of the geological formation.

In a second implementation, a non-transitory, computer-readable medium stores one or more instructions executable by a computer system to perform operations including the following. A rock type of a geological formation of a reservoir is determined using petrophysical data. The transmissible sublayers of the reservoir are determined by grouping the petrophysical data into different subset transmissible layers based on cut-off criteria. Net transmissible reservoir footage for the transmissible sublayers are generated based on averages of parameters for minimum and maximum measured depths. Potential stages for the reservoir are determined using a conditional formatting on the transmissible reservoir footage. Potential perforation cluster points selected based on the potential stages for the reservoir are received from input of an engineer.

The foregoing and other described implementations can each, optionally, include one or more of the following features:

A first feature, combinable with any of the following features, where determining the petrophysical data includes processing logging-while-drilling (LWD) data to include resistivity data, density data, and neutron porosity data.

A second feature, combinable with any of the previous or following features, where the operations further include: providing, for presentation to the engineer, a history of offset wells' completion and performance to adjust for stage length, a number of clusters, and clusters' positions relative to a transmissible net reservoir coverage defined by the transmissible reservoir footage; and providing, for presentation to the engineer, the number of clusters required to effectively stimulate stages of the reservoir.

A third feature, combinable with any of the previous or following features, where the operations further include receiving, from input of the engineer, manual adjustments to the number of clusters to meet staging requirement in terms of stage spacing, number of clusters, and plug depth to enable smooth stimulation operations.

A fourth feature, combinable with any of the previous or following features, where the operations further include determining whether the potential stages need validation.

A fifth feature, combinable with any of the previous or following features, where the operations further include: in response to determining that the potential stages need validation, performing an optimization on the transmissible layers.

A sixth feature, combinable with any of the previous or following features, where determining the rock type includes determining a rock testability index (RTI) including: receiving, by a computer system, petrophysical data of the geological formation at a particular rate, the petrophysical data measured at each depth of a plurality of depths from a surface of the Earth; for each depth of the plurality of depths, determining, using the computer system, a rock testability index (RTI) for the geological formation, the RTI indicating a probability of success for performing a hydrocarbon fluid formation test at each depth, the determining of the RTI including: generating, using the computer system, the RTI, the generating including normalizing a rock type of the geological formation; and adjusting, using the computer system, the RTI based on a correspondence of the petrophysical data to hydrocarbon productivity; and generating, using a display device of the computer system, a visual representation of the RTI at the particular rate, the visual representation indicating a potential hydrocarbon productivity of the geological formation.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. A rock type of a geological formation of a reservoir is determined using petrophysical data. The transmissible sublayers of the reservoir are determined by grouping the petrophysical data into different subset transmissible layers based on cut-off criteria. Net transmissible reservoir footage for the transmissible sublayers are generated based on averages of parameters for minimum and maximum measured depths. Potential stages for the reservoir are determined using a conditional formatting on the transmissible reservoir footage. Potential perforation cluster points selected based on the potential stages for the reservoir are received from input of an engineer.

The foregoing and other described implementations can each, optionally, include one or more of the following features:

A first feature, combinable with any of the following features, where determining the petrophysical data includes processing logging-while-drilling (LWD) data to include resistivity data, density data, and neutron porosity data.

A second feature, combinable with any of the previous or following features, where the operations further include: providing, for presentation to the engineer, a history of offset wells' completion and performance to adjust for stage length, a number of clusters, and clusters' positions relative to a transmissible net reservoir coverage defined by the transmissible reservoir footage; and providing, for presentation to the engineer, the number of clusters required to effectively stimulate stages of the reservoir.

A third feature, combinable with any of the previous or following features, where the operations further include receiving, from input of the engineer, manual adjustments to the number of clusters to meet staging requirement in terms of stage spacing, number of clusters, and plug depth to enable smooth stimulation operations.

A fourth feature, combinable with any of the previous or following features, where the operations further include determining whether the potential stages need validation.

A fifth feature, combinable with any of the previous or following features, where the operations further include: in response to determining that the potential stages need validation, performing an optimization on the transmissible layers.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method performed by a computer system, the computer-implemented method comprising:
    determining, using petrophysical data, a rock type of a geological formation of a reservoir;
    determining transmissible sublayers of the reservoir by grouping the petrophysical data into different subsets of transmissible layers based on cut-off criteria;
    generating, using at least a rock type injectivity model, net transmissible reservoir footage for the transmissible sublayers based on averages of parameters for minimum and maximum measured depths, wherein the net transmissible reservoir footage defines transmissible reservoir footage intervals indicating positions to locate perforations in the reservoir to aid with injectivity and to stimulate stages of the reservoir;
    determining potential stages for the reservoir using a conditional formatting on the net transmissible reservoir footage, wherein the conditional formatting identifies the potential stages satisfying a given criterion for the rock type and the net transmissible reservoir footage;
    receiving, from input of an engineer, potential perforation cluster points selected based on the potential stages for the reservoir; and
    using the potential perforation cluster points during stimulation operations of the reservoir, including positioning clusters of the potential perforation cluster points used during simulation of the reservoir.

2. The computer-implemented method of claim 1, wherein determining the petrophysical data includes processing logging-while-drilling (LWD) data to include resistivity data, density data, and neutron porosity data.

3. The computer-implemented method of claim 1, further comprising:
    providing, for presentation to the engineer, a history of offset wells' completion and performance to adjust for stage length, a number of clusters, and clusters' positions relative to a transmissible net reservoir coverage defined by the net transmissible reservoir footage;
    providing, for presentation to the engineer, the number of clusters required to effectively stimulate stages of the reservoir;
    receiving, in response to providing the history and number of clusters, input of the engineer; and
    adjusting, based on the input of the engineer, a stage length, a number of clusters, and clusters' positions relative to a transmissible net reservoir coverage defined by the net transmissible reservoir footage.

4. The computer-implemented method of claim 3, further comprising:
    receiving, from input of the engineer, manual adjustments to the number of clusters to meet staging requirement in terms of stage spacing, number of clusters, and plug depth to enable smooth stimulation operations.

5. The computer-implemented method of claim 1, further comprising:
    determining whether the potential stages need validation.

6. The computer-implemented method of claim 5, further comprising:
in response to determining that the potential stages need validation, performing an optimization on the different subsets of transmissible layers.

7. The computer-implemented method of claim 1, wherein determining the rock type includes determining a rock testability index (RTI) comprising:
receiving, by a computer system, petrophysical data of the geological formation at a particular rate, the petrophysical data measured at each depth of a plurality of depths from a surface of the Earth;
for each depth of the plurality of depths, determining, using the computer system, a rock testability index (RTI) for the geological formation, the RTI indicating a probability of success for performing a hydrocarbon fluid formation test at each depth, the determining of the RTI comprising:
generating, using the computer system, the RTI, the generating comprising normalizing a rock type of the geological formation; and
adjusting, using the computer system, the RTI based on a correspondence of the petrophysical data to hydrocarbon productivity; and
generating, using a display device of the computer system, a visual representation of the RTI at the particular rate, the visual representation indicating a potential hydrocarbon productivity of the geological formation.

8. A non-transitory, computer-readable medium storing one or more instructions executable by a computer system to perform operations comprising:
determining, using petrophysical data, a rock type of a geological formation of a reservoir;
determining transmissible sublayers of the reservoir by grouping the petrophysical data into different subsets of transmissible layers based on cut-off criteria;
generating, using at least a rock type injectivity model, net transmissible reservoir footage for the transmissible sublayers based on averages of parameters for minimum and maximum measured depths, wherein the net transmissible reservoir footage defines transmissible reservoir footage intervals indicating positions to locate perforations in the reservoir to aid with injectivity and to stimulate stages of the reservoir;
determining potential stages for the reservoir using a conditional formatting on the net transmissible reservoir footage, wherein the conditional formatting identifies the potential stages satisfying a given criterion for the rock type and the net transmissible reservoir footage;
receiving, from input of an engineer, potential perforation cluster points selected based on the potential stages for the reservoir; and
using the potential perforation cluster points during stimulation operations of the reservoir, including positioning clusters of the potential perforation cluster points used during simulation of the reservoir.

9. The non-transitory, computer-readable medium of claim 8, wherein determining the petrophysical data includes processing logging-while-drilling (LWD) data to include resistivity data, density data, and neutron porosity data.

10. The non-transitory, computer-readable medium of claim 8, the operations further comprising:
providing, for presentation to the engineer, a history of offset wells' completion and performance to adjust for stage length, a number of clusters, and clusters' positions relative to a transmissible net reservoir coverage defined by the net transmissible reservoir footage;
providing, for presentation to the engineer, the number of clusters required to effectively stimulate stages of the reservoir;
receiving, in response to providing the history and number of clusters, input of the engineer; and
adjusting, based on the input of the engineer, a stage length, a number of clusters, and clusters' positions relative to a transmissible net reservoir coverage defined by the net transmissible reservoir footage.

11. The non-transitory, computer-readable medium of claim 10, the operations further comprising:
receiving, from input of the engineer, manual adjustments to the number of clusters to meet staging requirement in terms of stage spacing, number of clusters, and plug depth to enable smooth stimulation operations.

12. The non-transitory, computer-readable medium of claim 8, the operations further comprising:
determining whether the potential stages need validation.

13. The non-transitory, computer-readable medium of claim 12, the operations further comprising:
in response to determining that the potential stages need validation, performing an optimization on the different subsets of transmissible layers.

14. The non-transitory, computer-readable medium of claim 8, wherein determining the rock type includes determining a rock testability index (RTI) comprising:
receiving, by a computer system, petrophysical data of the geological formation at a particular rate, the petrophysical data measured at each depth of a plurality of depths from a surface of the Earth;
for each depth of the plurality of depths, determining, using the computer system, a rock testability index (RTI) for the geological formation, the RTI indicating a probability of success for performing a hydrocarbon fluid formation test at each depth, the determining of the RTI comprising:
generating, using the computer system, the RTI, the generating comprising normalizing a rock type of the geological formation; and
adjusting, using the computer system, the RTI based on a correspondence of the petrophysical data to hydrocarbon productivity; and
generating, using a display device of the computer system, a visual representation of the RTI at the particular rate, the visual representation indicating a potential hydrocarbon productivity of the geological formation.

15. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:
determining, using petrophysical data, a rock type of a geological formation of a reservoir;
determining transmissible sublayers of the reservoir by grouping the petrophysical data into different subsets of transmissible layers based on cut-off criteria;
generating, using at least a rock type injectivity model, net transmissible reservoir footage for the transmissible sublayers based on averages of parameters for minimum and maximum measured depths, wherein the net transmissible reservoir footage defines transmissible reservoir footage intervals indicating positions to locate perforations in the reservoir to aid with injectivity and to stimulate stages of the reservoir;

determining potential stages for the reservoir using a conditional formatting on the net transmissible reservoir footage, wherein the conditional formatting identifies the potential stages satisfying a given criterion for the rock type and the net transmissible reservoir footage;

receiving, from input of an engineer, potential perforation cluster points selected based on the potential stages for the reservoir; and using the potential perforation cluster points during stimulation operations of the reservoir, including positioning clusters of the potential perforation cluster points used during simulation of the reservoir.

16. The computer-implemented system of claim 15, wherein determining the petrophysical data includes processing logging-while-drilling (LWD) data to include resistivity data, density data, and neutron porosity data.

17. The computer-implemented system of claim 15, the operations further comprising:

providing, for presentation to the engineer, a history of offset wells' completion and performance to adjust for stage length, a number of clusters, and clusters' positions relative to a transmissible net reservoir coverage defined by the net transmissible reservoir footage;

providing, for presentation to the engineer, the number of clusters required to effectively stimulate stages of the reservoir;

receiving, in response to providing the history and number of clusters, input of the engineer; and adjusting, based on the input of the engineer, a stage length, a number of clusters, and clusters' positions relative to a transmissible net reservoir coverage defined by the net transmissible reservoir footage.

18. The computer-implemented system of claim 17, the operations further comprising:

receiving, from input of the engineer, manual adjustments to the number of clusters to meet staging requirement in terms of stage spacing, number of clusters, and plug depth to enable smooth stimulation operations.

19. The computer-implemented system of claim 15, the operations further comprising:

determining whether the potential stages need validation.

20. The computer-implemented system of claim 19, the operations further comprising:

in response to determining that the potential stages need validation, performing an optimization on the different subsets of transmissible layers.

* * * * *